United States Patent
Allen et al.

(12) 
(10) Patent No.: US 6,529,577 B1
(45) Date of Patent: Mar. 4, 2003

(54) SYSTEM FOR, AND METHOD OF, IRRADIATING ARTICLE WITH X-RAY BEAM

(75) Inventors: John Thomas Allen, San Diego, CA (US); Gary K. Loda, Pleasanton, CA (US); George Michael Sullivan, Jr., San Diego, CA (US); Colin Brian Williams, La Jolla, CA (US)

(73) Assignee: Surebeam Corporation, San Diego, CA (US)

( * ) Notice: Subject to any disclaimer, the term of this patent is extended or adjusted under 35 U.S.C. 154(b) by 45 days.

(21) Appl. No.: 09/753,287

(22) Filed: Dec. 29, 2000

(51) Int. Cl.[7] .................................................. G21K 5/10
(52) U.S. Cl. ........................ 378/69; 378/68; 250/453.11
(58) Field of Search .............................. 378/69, 68, 20, 378/64; 250/455.11, 453.11, 454.11

(56) References Cited

U.S. PATENT DOCUMENTS

| | | | |
|---|---|---|---|
| 4,852,138 A | * | 7/1989 | Bergeret et al. ....... 250/453.11 |
| 4,866,281 A | * | 9/1989 | Bosshard ............... 250/453.11 |
| 6,294,791 B1 | * | 9/2001 | Williams et al. ....... 250/453.11 |

* cited by examiner

Primary Examiner—Robert H. Kim
Assistant Examiner—Pamela R. Hobden
(74) Attorney, Agent, or Firm—Fulwider Patton, et al.; Ellsworth R. Roston

(57) ABSTRACT

A first support structure disposes articles relative to a radiation beam, preferably x-rays, to obtain an irradiation of the articles. A second support structure disposes articles relative to the beam and to the articles on the first structure to obtain an irradiation of the articles by radiation passing from the accelerator through the articles on the first structure. A mechanism transfers the particles on the first structure to the second structure, after the irradiation of the articles on the first structure, to obtain the irradiation of the articles on the second structure. Each of the first and second structures may provide for an irradiation of articles initially through first sides of the articles and subsequently through second sides of the articles opposite to first sides. The irradiation of the first sides of the articles on the first and second support structures are preferably synchronous from a time standpoint as are the irradiation of the second sides of the articles on the structures. The transfer mechanism provides for the transfer of the articles from the first structure to the second structure after the synchronous irradiation of the second sides of the articles on the support structures. A loading area transfers articles to the first structure for an irradiation of the articles by the x-ray beam. A unloading area provides for transfer of articles from the second structure after the irradiation of the opposite sides of the articles on the second structure.

38 Claims, 1 Drawing Sheet

SYSTEM FOR, AND METHOD OF, IRRADIATING ARTICLE WITH X-RAY BEAM

This invention relates to apparatus for, and methods of, sterilizing articles such as food, drugs and medical instruments and implements. The invention particularly relates to apparatus for, and methods of, sterilizing articles which have a relatively great thickness.

BACKGROUND OF THE PREFERRED EMBODIMENT OF THE INVENTION

It has been known for some time that drugs and medical instruments and implements have to be sterilized so that they will not cause patients to become ill from harmful bacteria when they are applied to the patients. Systems have accordingly been provided for sterilizing drugs and medical instruments and implements. The drugs and the medical instruments and implements have then beam stored in sterilized packages until they have been ready to be used.

In recent years, it has been discovered that foods can carry harmful bacteria if they are not processed properly or, even if they are processed properly, that the foods can harbor such harmful bacteria if they are not stored properly or retained under proper environmental conditions such as temperature. Some of these harmful bacteria can even be deadly.

For example, harmful bacteria have been discovered in recent years in hamburgers and by one of the large hamburger chains. Such harmful bacteria has caused a number of purchasers of hamburgers from stores in the chain to become sick. As a result of the incident and several other similar incidents, it is now recommended that hamburgers should be cooked to a medium state rather than a medium rare or rare state.

Similarly, harmful bacteria have been found to exist in many chickens that are sold to the public. As a result of a number of incidents which have recently occurred, it is now recommended that all chickens be cooked so that no blood is visible in the cooked chickens.

To prevent incidents such as discussed in the previous paragraphs from occurring, various industries have now started to plan to sterilize foods before the foods are sold to the public. This is true, for example, of hamburgers and chickens. It is also true of fruits, particularly fruits which are imported from foreign countries.

In previous years, gamma rays have generally been the preferred medium for sterilizing various articles. The gamma rays have been obtained from a suitable material such as cobalt and have been directed to the articles to be sterilized. The use of gamma rays has offered certain disadvantages. One disadvantage is that sterilization by gamma rays is slow. Another disadvantage is that sterilization by gamma rays is not precise. This results from the fact that the strength of the source (e.g., cobalt) of the gamma rays decreases over a period of time and that the gamma rays cannot be directed in a sharp beam to the article to be sterilized. This prevents all of the gamma rays from being useful in sterilizing the articles.

In recent years, electron beams have been directed to articles to sterilize the articles. Electron beams have certain advantages over the prior use of gamma rays to sterilize objects. One advantage is that sterilization by electron beams is fast. Another advantage is that sterilization by electron beams is relatively precise. Sterilization by electron beams is relatively precise because the strength of the electron beam remains substantially constant even when the electron beam continues to be generated over a long period of time.

Sterilization by electron beams has a limitation which sometimes may possibly be significant. Electrons in the electron beams constitute mass. As the electrons in the beam travel through the article to sterilize the article, they are slowed and eventually stopped by the mass of the article. This limits the thickness of articles which can be sterilized by electron beams.

X-rays have been used to sterilize articles. X-rays are advantageous in that they have no mass. The x-rays are in the form of electromagnetic energy which penetrates the articles to be sterilized. Since the x-rays have no mass, they are effective in sterilizing articles with significant thicknesses. These significant thicknesses are considerably greater than the thicknesses of the articles which can be sterilized by other forms of energy such as electron beams.

There is one significant disadvantage, among others, in the use of x-rays to sterilize an article. This results from the fact that a considerable amount of energy remains in the x-rays after the x-rays have passed through the article. The energy remaining in the x-rays after the passage of the x-rays through the article has represented wasted energy because they are not used for any useful purpose.

BRIEF DESCRIPTION OF A PREFERRED EMBODIMENT OF THE INVENTION

In a preferred embodiment of the invention, articles having a considerable width are subjected to radiation. The widths of the articles are so great that x-rays are preferably used to provide the radiation. In a preferred embodiment of the invention, all of the x-ray energy is used to irradiate the articles, in contrast to the embodiments in the prior art. All of the x-ray energy is used efficiently in this manner without reducing the number of units which are processed per unit of time.

In the preferred embodiment, a first support structure disposes articles relative to a radiation beam, preferably x-rays, to obtain an irradiation of the articles by radiation passing from the beam through the articles on the first structure. A second support structure disposes articles relative to the beam and to the articles on the first structure to obtain an irradiation of the articles by radiation passing from the accelerator through the articles on the first structure. A mechanism transfers the articles on the first structure to the second structure, after the irradiation of the articles on the first structure, to obtain the irradiation of the articles on the second structure.

Each of the first and second structures may provide for an irradiation of the articles initially through first sides of the articles and subsequently through second sides of the articles opposite to the first sides. The irradiation of the first sides of the articles on the first and second support structures are preferably synchronous from a time standpoint as are the irradiations of the second sides of the articles on the structures. The transfer mechanism provides for the transfer of the articles from the first structure to the second structure after the synchronous irradiation of the second sides of the articles in the support structure.

A loading area transfers articles to the first structure for an irradiation of the articles by the x-ray radiation. An unloading area provides for a transfer of articles from the second structure after the irradiation of the opposite sides of the articles in the second structure.

BRIEF DESCRIPTION OF THE DRAWING

The single FIGURE is a schematic diagram of a preferred embodiment of the invention for irradiating articles with a radiation beam, preferably x-rays.

DETAILED DESCRIPTION OF A PREFERRED EMBODIMENT OF THE INVENTION

Figure 1:
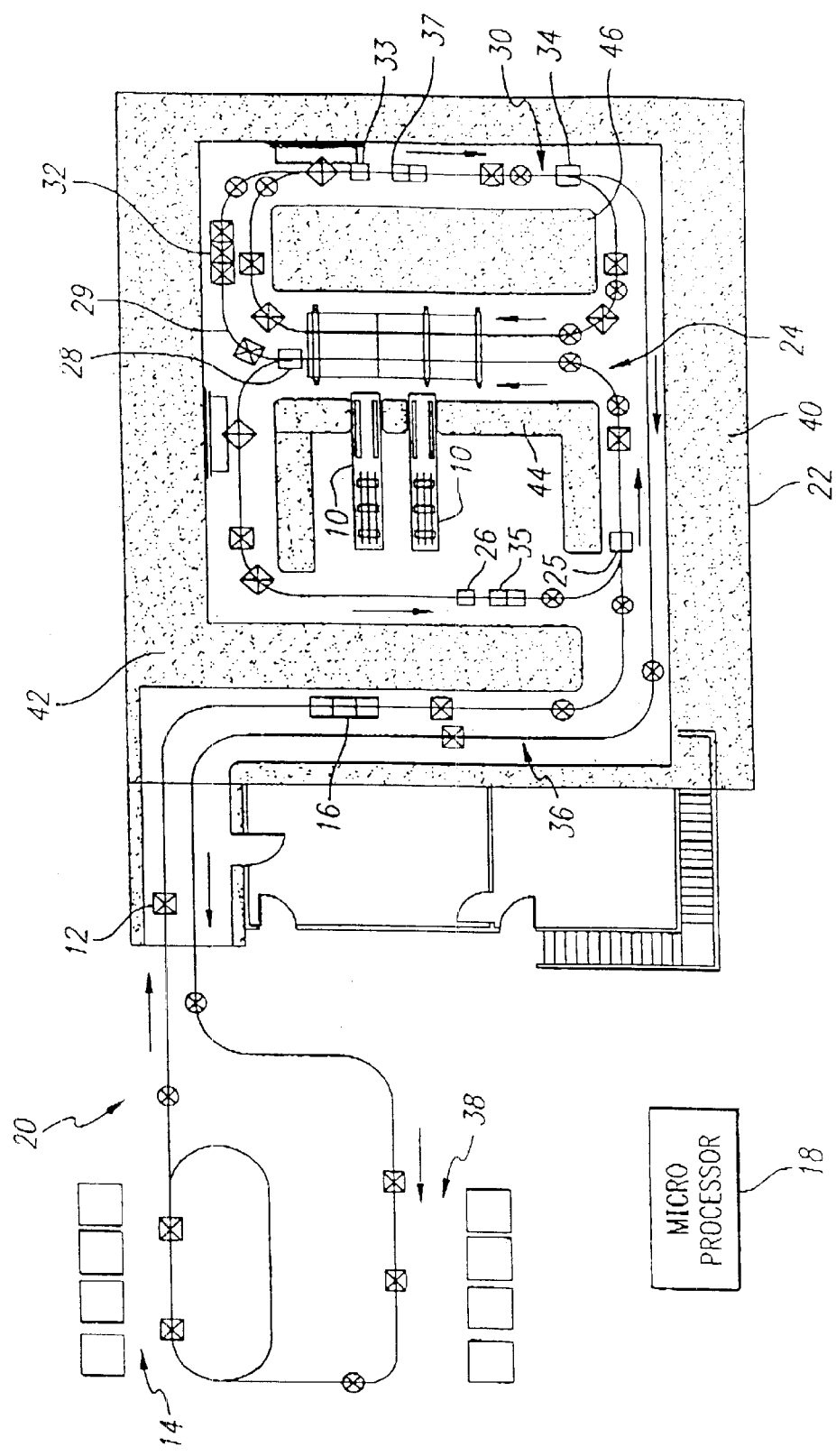

Systems are now being adopted for sterilizing various types of articles including food products by radiating the food products. When the food products are relatively narrow, electron beams are now generally being used. The electron beams have especial utility when the articles being irradiated have a thickness within particular limits. For example, electron beams are used to irradiate flat hamburger patties weighing one-quarter of a pound (¼ lb) or one-half of a pound (½ lb).

Electron beams are generally not effective in irradiating articles having a relatively great width. This results from the fact that the electron beams have weight. This weight causes the electron beams to become decelerated as they pass through the article being irradiated. Thus, the interior of the articles is not irradiated. This is true even when the electron beams enter into the article from two (2) opposite sides of the articles in two (2) successive movements of the article past the radiator.

For articles of considerable thicknesses, x-rays are often used to irradiate the articles. X-rays are advantageous because they constitute electromagnetic waves which do not have any mass. As a result, the x-rays are not slowed as they pass through the articles being sterilized. A disadvantage is that a considerable amount of the x-ray energy is not utilized in sterilizing articles when the thickness of the articles is (a) above the range where the articles can be sterilized by electron beams (b) but below the range where the full intensity of the radiation from the x-rays can be efficiently utilized in sterilizing the articles.

The preferred embodiment of this invention provides for an efficient use of the full intensities of x-rays in sterilizing relatively thick articles. This efficient use is provided by subjecting the articles initially to the full intensity of the x-ray radiation from an accelerator and subsequently to the reduced intensity remaining after the initial radiation of the articles. The initial and subsequent radiations are provided in a way so that the number of articles radiated per unit of time is not reduced relative to the number of units which are radiated per the unit of time when only the initial radiations are provided.

In a preferred embodiment of the invention, a beam of radiation, preferably x-rays, is provided by accelerators generally indicated at 10. The x-rays may be formed in a conventional manner well known in the art. For example, the x-rays may be formed by impinging electrons in an electron beam on a Brehm stalling member such as a member made from titanium. This is well known in the prior art.

The beam of x-rays is directed to articles 12 which are transferred from a loading area generally indicated at 14. The articles 12 may have a thickness which is greater than the maximum thickness at which the articles can be irradiated by an electron beam. The articles 12 may be stacked in a queue 16 at a position between the loading area 14 and the position at which the articles are irradiated by the accelerators 10. The release of successive ones of the articles 12 from the queue 16 may be controlled by a microprocessor 18. The loading area 14, the queue 16 and the microprocessor 18 may be constructed in a conventional manner well known to persons of ordinary skill in the art.

The articles 12 may be moved by a conveyor system, generally indicated at 20, from the loading area 14 to the position at which the articles are irradiated by the radiation, preferably xrays, from the accelerator 10. The irradiation of the articles 12 is preferably provided within a closed chamber 22. The chamber 20 may be made from a suitable material such as concrete or steel to insulate the space outside of the chamber from the radiation within the chamber.

The articles 12 on the conveyor system 20 are transferred to a conveyor system, generally indicated at 24, which is preferably disposed in the form of a loop within the chamber 22. Preferably the conveyor system 24 may be constructed in a conventional manner and is preferably provided in the form of a closed loop. The articles 12 are moved on the conveyor system 24 past the accelerators 10 which direct the radiation from the accelerator against a first side of the articles.

The articles 12 are then moved on the conveyor system 24 to apparatus 26 which rotates the articles in a conventional manner through an angle of substantially 180°. In this way, radiation from the accelerators 10 will be directed against a second side of the articles opposite the first side when the articles are directed by the conveyor system 24 for a second time past the radiation from the accelerators 10.

A switch 25 is provided with first and second states of operation. In the first state of operation, the switch 25 provides for a transfer of the loading article 12 in the queue 16 to the conveyor system 24. In the second state of operation, the switch 25 provides for the movement of the article on the conveyor system 24 past the accelerators 10 in a second pass to obtain an irradiation of the x-ray beam through the second side of the article 12 after the article has been rotated through an angle of substantially 180°. The operation at each instant of the switch 25 in the respective one of the first and second states is controlled by the microprocessor 18. As will be appreciated, the switch 25 operates in the first state for each article 12 to provide for a transfer of the article from the conveyor system 20 to the conveyor system 24. The switch 25 subsequently operates in the second state to provide for the movement of the article 12 a second time past the accelerators 10 to obtain an irradiation of the second side of the article. The times for the operation of the switch 25 in the first and second states are controlled by the microprocessor 18.

A switch 28 is provided on the conveyor system 24. The switch 28 may be provided with first and second states of operation under the control of the microprocessor 18. In the first state of operation, the switch 28 provides for the movement of the articles 12 past the apparatus 26 for rotating the articles through the angle of 180°. In the second state of operation, the switch 28 provides for the transfer of the articles 12 from the conveyor system 24 to a conveyor system, generally indicated at 30. The operation of the switch 28 in the first and second states may be controlled by the microprocessor 18. The switch 28 is initially operated in the first state for each of the articles 12 under the control of the microprocessor 18 and is subsequently operated in the second state for each of the articles 12 under the control of the microprocessor.

By providing the switch 28 in the first state of operation and rotating the article 12 through the angle of substantially 180°, the article 12 on the conveyor system 24 is irradiated from the second side of the article. This causes the cumulative irradiation at the different positions in the article 12 to be, for every position in the article, between maximum and minimum limits. The minimum limit of irradiation intensity is selected to insure that the cumulative irradiation at every position in the article 12 is at least at a level of intensity where harmful bacteria such as *E col* are destroyed. The maximum limit of irradiation intensity is selected so that beneficial bacteria in the article will not be destroyed.

The thickness of the article 12 may sometimes be above a value where the cumulative intensity of the radiation of the article at some positions in the article will be above the maximum intensity of the article irradiation for optimal results even though the intensity of the irradiation of the article at other positions is between the maximum and minimum limits. Under such circumstances, a member may be positioned between the accelerator 10 and the article 12 to absorb some of the radiation intensity from the accelerator at the positions in the article where the intensity of the radiation is above the maximum limit. In this way, the cumulative intensity of the radiation at every position in the articles is between the minimum and maximum optimal values. A system for adjusting the intensity of the irradiation in the article 12 to intensities between the minimum and maximum values is disclosed and claimed in U.S. patent application listing Gary K. Loda and Richard C. Miller as joint inventors and relating to a SYSTEM FOR, AND METHOD OF, IRRADIATING AN OBJECT WITH AN OPTIMAL AMOUNT OF RADIATION. Patent application Ser. No. 09/710,930 is assigned of record to the assignee of record of this patent application.

Since x-rays can penetrate the article 12 through relatively great thicknesses, the x-rays can often pass from one side of the article through the article and emerge from the opposite side of the article with a significant intensity. Until now, such x-ray energy has been lost since no use has been made of such energy. This application provides a system for, and method of, utilizing the significant amount of energy passing through each of the articles 12 so as to irradiate the article with this significant amount of energy. In this way, substantially all of the x-ray energy in the radiation beam from the accelerators 10 is used to irradiate the article 12. In irradiating the article 12 twice in this manner, the intensity of the radiation beam from the accelerator 10 can be reduced, thereby minimizing the cost of the accelerator and the cost of providing radiation from the accelerator, when the irradiations of the articles 12 on the conveyor systems 24 and 30 are cumulatively at the desired intensity.

To utilize the x-ray energy passing through the article 12 on the conveyor system 30, the switch 28 is operated in the second state after the article has been rotated through an angle of substantially 180° by the apparatus 26 and the second side of the article has been irradiated by the x-ray beam from the accelerators 10. In the second state of operation, the switch 28 passes the article 12 to the second conveyor system 30. The second conveyor system 30 is disposed in the thick amber 22. The second conveyor system 30 may be disposed in a loop, preferably closed, similar to the configuration of the conveyor system 24. However, as shown at 29 in the single FIGURE, the article 12 may have to travel through a portion of a loop after it has been transferred from the conveyor 24 and before it reaches the conveyor system 30.

At substantially the same time that the article 12 on the first conveyor system 24 is transferred to the second conveyor system 30, an article 12 in the loading area 14 is transferred to the queue 16. At substantially the same time, the leading article 12 in the queue 16 is transferred to the conveyor system 24. The movement of the article 12 from the first conveyor system 24 to the position on the second conveyor system 30 for receiving the x-ray beam passing from the accelerators 10 through the article on the first conveyor system 24 is synchronized with the movement of the article from the queue 16 to the position on the first conveyor system for receiving the x-ray beams from the accelerators 10. This synchronization is provided by the operation of a queue 32 on the second conveyor system. The queue 32 stores articles transferred from the first conveyor system 24 and releases the leading article in the queue for movement to the position for receiving the x-ray beam passing from the accelerators 10 through the article on the first conveyor system.

The microprocessor 18 synchronizes the movement of the article 12 from the queue 32 to the position for receiving the x-ray beam passing from the accelerator 10 through the article on the first conveyor system 24. The microprocessor 18 also synchronizes the movement of the article from the queue 16 in the first conveyor system 24 to the position for receiving the radiation from the accelerators 10. In this way, the x-ray beam from the accelerators 10 passes through the article 12 on the first conveyor system 24 and then through the article on the second conveyor system 30.

The synchronization by the microprocessor 18 between the movement of each article on the first conveyor system 24 and the article on the second conveyor system 30 is even more sophisticated than indicated in the previous paragraph. This even more sophisticated synchronization is provided by the microprocessor 18. Under the control of the microprocessor 18, the first side of the article 12 on the conveyor system 24 moves past the radiation from the accelerators 10 at the same time that the first side of the article on the conveyor system 30 moves past the radiation passing from the accelerators through the article on the conveyor system 24. In like manner, the second side of the article 12 on the conveyor system 24 moves past the radiation from the accelerators 12 at the same time that the second side of the article on the conveyor system 30 moves past the radiation passing from the accelerators through the article on the conveyor system 24. The synchronous movement of the second sides of the articles 12 on the conveyor systems 24 and 30 past the radiation from the accelerators 10 may be facilitated by providing queues 35 and 37 respectively on the conveyor systems 24 and 30 and by having the microprocessor 18 synchronize the release of the articles from the queues.

An apparatus 33 is provided for rotating each article 12 on the conveyor system 30 through an angle of 180° after the article has moved a first time past the position for receiving irradiation on the first side of each article on the conveyor system 30 from the accelerators 10 and before the article has moved a second time past the position for receiving irradiation on the second side of the article on the conveyor system 30 from the accelerators 10. The operation of the apparatus 33 in rotating each article 12 through an angle of 180° is controlled by the microprocessor 18.

A switch 34 having first and second states of operation is provided on the conveyor system 30 at a position past the position where each article 12 on the conveyor system is irradiated with the radiation passing through the article on the conveyor system 24 from the accelerators 10. In the first state, the switch 34 provides for the movement of each article 12 on the conveyor system 30 past the position where the radiation from the accelerator 10 passes through the articles on the conveyor system 24. In the second state, the switch 34 provides for the passage of the articles on the conveyor system 30 to a conveyor system generally indicated at 36. The conveyor system 36 moves the articles 12 to an unloading area generally indicated at 38. The articles 12 are removed from the conveyor system 36 at the unloading area 38.

The operation of the switch 34 in the first and second state is controlled by the microprocessor 18. The switch 34 initially operates in the first state to move each article 12 on the conveyor system 30 past the position for irradiating the article with radiation passing through the article on the conveyor system 24 from the accelerator 10. The switch 34 operates in the first state twice so that the article 12 can move twice past the position for receiving radiation from the accelerators 10, the first time for receiving radiation on the first side of the article 10 and the second time for receiving radiation on the second side of the article. The switch 34 subsequently operates in the second state for transferring each article 12 from the conveyor system 30 to the conveyor system 36 and then to the unloading area 38 after the first and second sides of the article on the conveyor system 30 have been irradiated.

Radiation shielding material is disposed within the chamber 22 in a strategic relationship to shield the articles 12 from radiation, except at the positions where they receive radiation from the accelerators 10, as the articles move through the chamber 22. For example, the chamber 22 may be defined by radiation shielding material 40. The shielding material 40 may be made from concrete. A radiation shielding member 42 made from a suitable material such as concrete may be disposed within the conveyor system 24 to prevent radiation from the accelerator 10 from passing to the conveyor systems 20 and 36, the loading area 14 and the unloading area 38. The radiation shielding member 42 also prevents radiation from the accelerator 10 from passing to the articles on the conveyor system 30 other than in the area where the radiation from the accelerator 10 passes directly to such articles. The radiation shielding member 42 may extend integrally from the radiation on shielding materials 40.

A radiation shielding member 44 made from a suitable material such as concrete may be disposed within the conveyor system 30 to shield the articles on the conveyor system from radiation except where the articles move past the position where the articles receive the radiation passing through the articles on the conveyor system 24 from the accelerators 10. A radiation shielding member 46 made from a suitable material such as concrete may be disposed within the conveyor system 30 to shield the articles 12 as they move on the conveyor system except in the portion of the conveyor system where the articles move past the accelerators 10.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. Apparatus for irradiating articles in sequence to sterilize the articles, including
   an accelerator for providing radiation in a particular direction,
   a first conveyor system for moving the articles in sequence past the accelerator for irradiating the articles with the radiation from the accelerator,
   a second conveyor system for receiving the articles in sequence from the first conveyor system after the irradiation of the articles with the radiation from the accelerator and for moving the articles in sequence past the accelerator and for irradiating the articles with the radiation passing from the accelerator, during the movement of the articles on the second conveyor system, through the articles on the first conveyor system to obtain further radiation of the articles.

2. Apparatus as set forth in claim 1 wherein
the accelerator provides x-ray radiation to the articles on the first and second conveyor systems.

3. Apparatus as set forth in claim 1 wherein
the first and second conveyor systems are operative to produce a movement of the articles on the second conveyor system past the radiation passing through the articles on the first conveyor system from the accelerator in synchronism with the movement of the articles on the first conveyor system past the radiation from the accelerator.

4. Apparatus as set forth in claim 1, including
a loading area disposed in displaced relationship to the first and second conveyor systems and constructed to hold the articles and transfer the articles in sequence from the loading area to the first conveyor system, and
an unloading area disposed in displaced relationship to the first and second conveyor systems and constructed to hold the articles and transfer the articles in sequence from the second conveyor system to the unloading area.

5. Apparatus as set forth in claim 1 wherein
each of the articles has first and second opposite sides and wherein
   the first conveyor system is constructed to move each of the articles first and second times past the radiation from the accelerator and to obtain an irradiation of the first side of the article in the first movement of the article past the radiation from the accelerator and to obtain an irradiation of the second side of the article in the second movement of the article past the radiation from the accelerator and wherein
   the second conveyor system is constructed to move each of the articles first and second times past the radiation from the accelerator and to obtain an irradiation or the first side of the article in the first movement of the article past the radiation from the accelerator and to obtain an irradiation of the second side of the article in the second movement of the article past the radiation from the accelerator.

6. Apparatus as set forth in claim 3 wherein
a loading area is disposed in displaced relationship to the first and second conveyor systems and is constructed to hold the articles and transfer the articles in sequence from the loading area to the first conveyor system and wherein
an unloading area is disposed in displaced relationship to the first and second conveyor systems and is constructed to hold the articles and transfer the articles in sequence from the second conveyor system to the unloading area and wherein
each of the articles has first and second opposite sides and wherein
   the first conveyor system is constructed to move each of the articles first and second times past the radiation from the accelerator and to obtain an irradiation of the first side of the article in the first movement of the article past the radiation from the accelerator and to obtain an irradiation of the second side of the article in the second movement of the article past the radiation from the accelerator and wherein
   the second conveyor system is constructed to move each of the articles first and second times past the radiation from the accelerator and to obtain an irradiation or the first side of the article in the first movement of the article past the radiation from the accelerator and to obtain an irradiation of the second side of the article in the second movement of the article past the radiation from the accelerator.

7. Apparatus as set forth in 6 wherein the accelerator provides x-ray radiation to the articles on the first and second conveyor systems.

8. Apparatus for irradiating articles in sequence to sterilize the articles, including an accelerator for providing a radiation beam in a particular direction, first support structure for disposing articles relative to the accelerator in the particular direction to obtain an irradiation of the articles by the accelerator, second support structure for disposing articles in the particular direction relative to the accelerator and the articles on the first support structure to obtain an irradiation of the articles by radiation passing in the particular direction from the accelerator through the articles on the first structure, and a transfer mechanism for transferring the articles on the first structure to the second structure after the irradiation of the articles on the first structure by radiation in the particular direction from the accelerator to obtain the irradiation of the articles on the second structure by the radiation passing in the particular direction from the accelerator through the articles on the first support structure.

9. Apparatus as set forth in claim 8, including a loading area for transferring articles to the first support structure to obtain an irradiation of the articles in the particular direction by the radiation from the accelerator, and an unloading area for providing for a transfer of articles from the second support structure after the irradiation of the articles in the particular direction on the second support structure.

10. Apparatus as set forth in claim 8 wherein the radiation in the particular direction to the articles on from the first support structure is in the form of a beam and wherein the first support structure positions the articles in the first support structure to receive the radiation beam in the particular direction from the accelerator and wherein the second support structure positions the articles on the second support structure to receive the radiation beam passing in the particular direction through the articles on the first support structure from the accelerator.

11. Apparatus as set forth in claim 8 wherein each of the articles has first and second opposite sides and wherein the first support structure provides for the passage of the radiation in the particular direction from the accelerator through the first and second opposite sides of the articles on the first support structure and wherein the second support structure provides for the passage, in the particular direction through the first and second opposite sides of each of the articles on the second support structure, of the radiation passing in the particular direction through the accelerator and the articles on the first support structure.

12. Apparatus as set forth in claim 9 wherein the radiation from the first support structure is in the form of a beam and wherein the first support structure positions the articles in the first support structure to receive the radiation beam in the particular direction from the accelerator and wherein the second support structure positions the articles on the second support structure to receive the radiation beam passing in the particular direction through the articles on the first structure from the accelerator and wherein each of the articles has first and second opposite sides and wherein the first support structure provides for the passage of the radiation in the particular direction from the accelerator through the first and second opposite sides of the articles on the first support structure and wherein the second support structure provides for the passage, in the particular direction through the first and second opposite sides of the articles on the second support structure, of the radiation passing in the particular direction through the accelerator and the articles on the first support structure.

13. Apparatus as set forth in claim 12 wherein the radiation is in the form of a beam of x-rays.

14. Apparatus as set forth in claim 8 wherein each of the articles has first and second opposite sides and wherein the first support structure provides for an irradiation of each of the articles on the first support structure in the particular direction from the accelerator initially through the side of the article and subsequently through the second side of the and wherein the second support structure provides for an irradiation of each of the articles in the particular direction on the second support structure initially through the first side of the article, and subsequently through the second side of the article on the first support structure.

15. Apparatus as set forth in claim 14 wherein the first and second support structures provide for the radiation from the accelerator to pass in the particular direction initially through the first sides of the articles respectively on the first and second support structures and subsequently through the second sides of the articles respectively on the first and second support structures and wherein the transfer mechanism provides for the transfer of the articles from the second support structure, and from the first support structure to the second support structure after the irradiation of the second sides of the articles on the first and second support structures.

16. Apparatus as set forth in claim 15, including, a loading area for transferring articles to the first support structure to obtain an irradiation of the articles in the particular direction by the radiation from the accelerator, and an unloading area for providing for a transfer of articles from the second structure after the irradiation of the first and second sides of the articles in the particular direction on the second support structure.

17. Apparatus as set forth in claim 16 wherein the radiation of the beam from the accelerator is in the form of x-rays.

18. A method of irradiating articles to sterilize the articles, including the steps of:

providing a beam of radiation, disposing first articles to become irradiated by the radiation beam, disposing second articles to become irradiated by the radiation beam after the passage of the radiation from the beam through the first articles, and providing for the first articles to become the second articles after the irradiation of the first articles with the beam of radiation.

19. A method as set forth in claim 18, including the steps of:

providing for additional articles to become the first articles in substitution for the first articles becoming the second articles.

20. A method as set forth in claim 18, including the step of:

providing for the second articles to become transferred from the position of irradiation by the passing of the beam of radiation through the first articles, and to be replaced by the first articles after the irradiation of the second articles with the beam of radiation passing through the first articles.

21. A method as set forth in claim 18 wherein the radiation from the beam constitutes x-rays.

22. A method as set forth in claim 18 wherein articles are transferred in sequence from a loading area to become the first articles and wherein the first articles are transferred in sequence to become the second articles after the first articles have been irradiated with the beam of radiation and wherein the second articles are transferred in sequence to an unloading area after they have been irradiated with the beam of radiation passing through the first articles.

23. A method as set forth in claim 22 wherein the transfer of articles in sequence from the loading area to become the first articles, the transfer of the first articles in sequence to become the second articles and the transfer of the second articles in sequence to the unloading area are synchronized.

24. A method as set forth in claim 23 wherein the synchronization provides for the first articles and the second articles to be aligned with the beam of radiation to obtain an irradiation of the first articles with the radiation of the beam and simultaneously to obtain the irradiation of the second articles with the radiation of the beam passing through the first articles.

25. A method of irradiating articles in sequence to sterilize the articles, including the steps of:

providing an accelerator for producing radiation, providing a first conveyor system for moving the articles in a first loop past the accelerator to obtain an irradiation of the articles with the radiation from the accelerator, providing a second conveyor system for moving the articles in a second loop past the accelerator to obtain an irradiation of the articles with the radiation from the accelerator, providing a disposition of the first and second conveyor systems relative to the accelerator to provide for the passage of the radiation from the accelerator through the articles on the first conveyor system and the articles on the second conveyor system, and transferring successive ones of the articles on the first conveyor system at each instant to the second conveyor system for the irradiation at that instant of the successive ones of the articles on the second conveyor system, after the previous irradiation of such successive ones of the articles on the first conveyor system, with the radiation passing from the accelerator at that instant through the articles on the first conveyor system.

26. A method as set forth in claim 25, including the steps of transferring successive ones of the articles in a loading area to the first conveyor system for the irradiation of the articles by the radiation from the accelerator, and transferring successive ones of the articles on the second conveyor system to an unloading area after the irradiation of the articles by the radiation passing through the articles on the first conveyor system from the accelerator.

27. A method as set forth in claim 25, including the step of:

synchronizing the movements of the articles on the first conveyor system past the radiation from the accelerator with the movement of the articles on the second conveyor system past the radiation passing through the articles on the first conveyor system from the accelerator.

28. A method as set forth in claim 27, including the step of:

synchronizing the transfer of the successive ones of the articles in the loading area to the first conveyor system and the transfer of the successive ones of the articles on the successive conveyor to the unloading area.

29. A method as set forth in claim 25 wherein the first conveyor system defines a first closed loop and wherein the first conveyor system provides first and second movements of the articles on the first conveyor system in the first closed loop past the radiation from the accelerator and provides for a rotation of the articles on the first conveyor system through an angle of substantially 180° between the first and second movements of the articles on the first conveyor system past the radiation from the accelerator and wherein the second conveyor system provides first and second movements of the articles in the first conveyor system past the radiation passing through the articles on the first conveyor system from the accelerator and provides for a rotation of the articles on the second conveyor system through an angle of substantially 180° between the first and second movements of the articles on the second conveyor system past the radiation from the source.

30. A method as set forth in claim 29 wherein successive ones of the articles in a loading area are transferred to the first conveyor system when the successive ones of the articles on the first conveyor system are transferred to the second conveyor system and wherein successive ones of the articles on the second conveyor system are transferred to an unloading area when successive ones of the articles on the first conveyor system are transferred to the second conveyor system.

31. A method as set forth in claim 30 wherein the first movement of the articles on the first conveyor system past the radiation from the accelerator is synchronized with the first movement of the articles on the second conveyor system past the radiation passing through the articles on the first conveyor system from the accelerator and wherein the second movement of the articles on the first conveyor system past the radiation from the accelerator is synchronized with the second movement of the articles on the second conveyor system past the radiation passing through the articles on the first conveyor system past the accelerator.

32. A method as set forth in claim 31 wherein the first sides of the articles are irradiated during the first movement of the articles past the radiation from the source and wherein the second sides of the articles are irradiated during the second movements of the articles past the radiation from the source.

33. A method of irradiating articles with an x-ray beam providing a first path for the irradiation of articles, disposing a second path for the irradiation of the article, providing x-rays for the irradiation of the articles in the first and second path, disposing the first and second paths relative to the x-rays to provide for the passages of the x-rays through the articles in the first and second paths, and providing a transfer of the articles in the first path to the second path after the irradiation of the articles in the first path.

34. A method as set forth in claim 33 wherein the movement of the articles in the first path to the position for irradiation by the x-rays of the articles in the first path is synchronized with the movement of the articles in the sum path to the position for irradiation of the articles in the second path.

35. A method as set forth in claim 33 wherein each of the articles in the first path is irradiated twice by the x-rays, once on a first side of the articles and the other time on a second side of the articles, and wherein each of the articles in the second path is irradiated twice by the x-rays, once on a first side of the articles and the other time on a second side of the articles.

36. A method as set forth in claim 35 wherein the irradiation of the first sides of the articles in the first and second paths by the x-rays and synchronized and wherein the irradiation of the second sides of the articles in the first and second paths is synchronized.

37. A method as set forth in claim 36 wherein the x-rays are disposed relative to the articles in the first and second paths to pass initially through the articles in the first path and then through the articles in the second paths.

38. A method as set forth in claim 36 wherein the articles in the first path are rotated through an angle of 180° between the first and second irradiations of the articles in the first path, the articles in the first path are transferred to the second path after the second irradiation of the articles in the first path and wherein the articles in the second path are related through an angle of 180° between the first and second irradiations of the articles in the second path.

\* \* \* \* \*